US012311083B2

(12) United States Patent
Childress et al.

(10) Patent No.: US 12,311,083 B2
(45) Date of Patent: May 27, 2025

(54) SYSTEMS AND METHODS FOR MANAGING AND PREDICTING POWER USAGE FOR ULTRAVIOLET LAMPS WITHIN AN ENVIRONMENT (71) Applicant: THE BOEING COMPANY, Chicago, IL (US)

(72) Inventors: Jamie J. Childress, Mercer Island, WA (US); Kevin S. Callahan, Shoreline, WA (US); Teresa A. King, Bothell, WA (US)

(73) Assignee: The Boeing Company, Chicago, IL (US)

( * ) Notice: Subject to any disclaimer, the term of this patent is extended or adjusted under 35 U.S.C. 154(b) by 615 days.

(21) Appl. No.: 17/703,186

(22) Filed: Mar. 24, 2022

(65) Prior Publication Data
US 2022/0362434 A1 Nov. 17, 2022

Related U.S. Application Data (60) Provisional application No. 63/186,839, filed on May 11, 2021.

(51) Int. Cl.
*A61L 9/20* (2006.01)
*B64D 11/00* (2006.01)
(52) U.S. Cl.
CPC ............ *A61L 9/20* (2013.01); *B64D 11/00* (2013.01); *A61L 2202/14* (2013.01)
(58) Field of Classification Search
CPC .......... A61L 9/20; A61L 2202/14; A61L 2/10; B64D 11/00; B64D 11/02; B64D 11/04; B64F 5/30; H02J 13/00016; H02J 3/003; H02J 3/06; H02J 13/00032; H02J 2203/10; G05B 13/026; H05B 47/10
See application file for complete search history.

(56) References Cited

U.S. PATENT DOCUMENTS

| | | | |
|---|---|---|---|
| 10,130,727 B1 | 11/2018 | Byrnes | |
| 10,301,806 B2 | 5/2019 | Childress | |
| 2018/0371733 A1 | 12/2018 | Childress | |
| 2019/0030195 A1 | 1/2019 | Hatti | |

FOREIGN PATENT DOCUMENTS

| | | |
|---|---|---|
| EP | 3315142 | 5/2018 |
| EP | 3659919 | 6/2020 |

OTHER PUBLICATIONS

Extended European Search Report for EP 22172170.7-1004, dated Sep. 12, 2022.
U.S. Appl. No. 17/352,724, filed Jun. 21, 2021.
U.S. Appl. No. 17/352,852, filed Jun. 21, 2021.
U.S. Appl. No. 17/352,819, filed Jun. 21, 2021.
U.S. Appl. No. 17/348,889, filed Jun. 16, 2021.
U.S. Appl. No. 17/336,595, filed Jun. 2, 2021.

*Primary Examiner* — Elmito Breval
(74) *Attorney, Agent, or Firm* — Joseph M. Butscher; The Small Patent Law Group LLC (57) ABSTRACT A power management system and method for a vehicle includes a plurality of ultraviolet (UV) light sub-systems within an internal cabin of the vehicle. A power management control unit is in communication with the plurality of UV light sub-systems. The power management control unit is configured to adaptively control power supplied to the plurality of UV light sub-systems based on power usage data. The power supplied to the plurality of UV light sub-systems changes. The power usage data includes information regarding adaptable power requirements for the plurality of UV light sub-systems.

22 Claims, 6 Drawing Sheets

SYSTEMS AND METHODS FOR MANAGING AND PREDICTING POWER USAGE FOR ULTRAVIOLET LAMPS WITHIN AN ENVIRONMENT

CROSS-REFERENCE TO RELATED APPLICATIONS

This application relates to and claims priority benefits from U.S. Provisional Patent Application No. 63/186,839, filed May 11, 2021, which is hereby incorporated by reference in its entirety.

FIELD OF THE DISCLOSURE

Embodiments of the present disclosure generally relate to systems and methods for managing and predicting power usage in relation to ultraviolet (UV) lamps, such as may be used to sanitize structures and areas within an environment, such as an internal cabin of a commercial aircraft or other vehicle.

BACKGROUND OF THE DISCLOSURE

Vehicles such as commercial aircraft are used to transport passengers between various locations. Systems are currently being developed to disinfect or otherwise sanitize surfaces within aircraft, for example, that use ultraviolet (UV) light.

The amount of power available in a vehicle is limited. A vehicle such as a commercial aircraft includes numerous powered sub-systems in addition to any potential UV sanitizing systems. A UV lamp operating at full capacity draws a particular amount of power.

SUMMARY OF THE DISCLOSURE

A need exists for a system and a method for managing power among UV lamps and other powered sub-systems of a vehicle. Further, a need exists for a system and a method for efficiently and effectively apportioning and predicting power usage in relation to various powered sub-systems and UV lamps of a vehicle.

With those needs in mind, certain embodiments provide a power management system for a vehicle (such as an aircraft). The power management system includes a plurality of ultraviolet (UV) light sub-systems within an internal cabin of the vehicle. A power management control unit is in communication with the plurality of UV light sub-systems. The power management control unit is configured to adaptively control power supplied to the plurality of UV light sub-systems based on power usage data. The power supplied to the plurality of UV light sub-systems changes. The power usage data includes information regarding adaptable power requirements for the plurality of UV light sub-systems.

In at least one embodiment, the power management control unit is configured to provide a different amount of power to at least two of the plurality of UV light sub-systems at a given time. That is, an amount of power can be provided to a first UV light sub-system that differs from the amount of power provided to a second UV light sub-system.

In at least one embodiment, the plurality of UV light sub-systems are within a plurality of different areas of the internal cabin. For example, the plurality of different areas comprise one or more of a lavatory, a galley, a passenger area, or a control area.

In at least one embodiment, the power management system also includes one or more powered sub-systems that differ from the UV light sub-systems. For example, the power management control unit is also in communication with the one or more powered sub-systems. The power management control unit also adaptively controls power supplied to the one or more powered sub-systems.

In at least one embodiment, the power management control unit adaptively controls the power supplied to the plurality of UV light sub-systems by one or both of reducing the power supplied to a first one of the plurality of UV light sub-systems or increasing the power supplied to a second one of the plurality of UV light sub-systems.

In at least one embodiment, a data bus is in communication with the power management control unit. The power management control unit receives the power usage data from the data bus.

In at least one embodiment, one or more presence sensors are within one or more of the plurality of areas. The power management control unit is in communication with the one or more presence sensors. The power management control unit adaptively controls the power supplied to the plurality of UV light sub-systems based on the power usage data and one or more presence signals received from the one or more presence sensors.

In at least one embodiment, a predictive power usage control unit is in communication with the power management control unit. The predictive power usage control unit receives power management data from the power management control unit. Thee predictive power usage control unit is configured to refine the power usage data based on the power management data. In at least one example, the predictive power usage control unit is remote from the vehicle.

As an example, the power usage data includes a prioritized list for powering essential and nonessential sub-systems.

Certain embodiments of the present disclosure provide a power management method for a vehicle. The power management method includes communicatively coupling a power management control unit with a plurality of ultraviolet (UV) light sub-systems within an internal cabin of the vehicle; and adaptively controlling, by the power management control unit, power supplied to the plurality of UV light sub-systems based on power usage data, wherein the power supplied to the plurality of UV light sub-systems changes, and wherein the power usage data includes information regarding adaptable power requirements for the plurality of UV light sub-systems.

Certain embodiments of the present disclosure provide a power management system for a vehicle. The power management system includes a plurality of ultraviolet (UV) light sub-systems within an internal cabin of the vehicle. The UV light sub-systems are configured to be provided power based on power usage data. The power usage data includes information regarding adaptable power requirements for the plurality of UV light sub-systems. A predictive power usage control unit is configured to receive power management data. The predictive power usage control unit is further configured to refine the power usage data based on the power management data.

DETAILED DESCRIPTION OF THE DISCLOSURE

The foregoing summary, as well as the following detailed description of certain embodiments will be better understood when read in conjunction with the appended drawings. As used herein, an element or step recited in the singular and preceded by the word "a" or "an" should be understood as not necessarily excluding the plural of the elements or steps. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular condition can include additional elements not having that condition.

As described herein, embodiments of the present disclosure provide power management systems and methods for an environment, such as an internal cabin of a vehicle. In at least one embodiment, predictive power and data management systems and methods for ultraviolet (UV) sub-systems include UV lamps allow for numerous UV sub-systems within the environment to coordinate power sharing based on need and/or demand. Embodiments of the present disclosure provide systems and methods for eliminating, minimizing, or otherwise reducing improper, ineffective, and inefficient use of power supplied to the UV sub-systems.

During various phases of a flight, for example, the UV lamp(s) may not need to be operating at full capacity. As an example, during takeoff and landing, UV lamps within certain areas of an internal cabin need not operate at full capacity as individuals may not be present. As a further example, individuals are not present within a lavatory during takeoff or landing. As such, UV disinfection during such phases of travel may not be necessary. However, a UV lamp within the lavatory may still be drawing power, despite not being needed to sanitize a surface during such time. The power provided to the UV lamp may be better used in relation to other devices, sub-systems, or the like within the aircraft.

Figure 1:
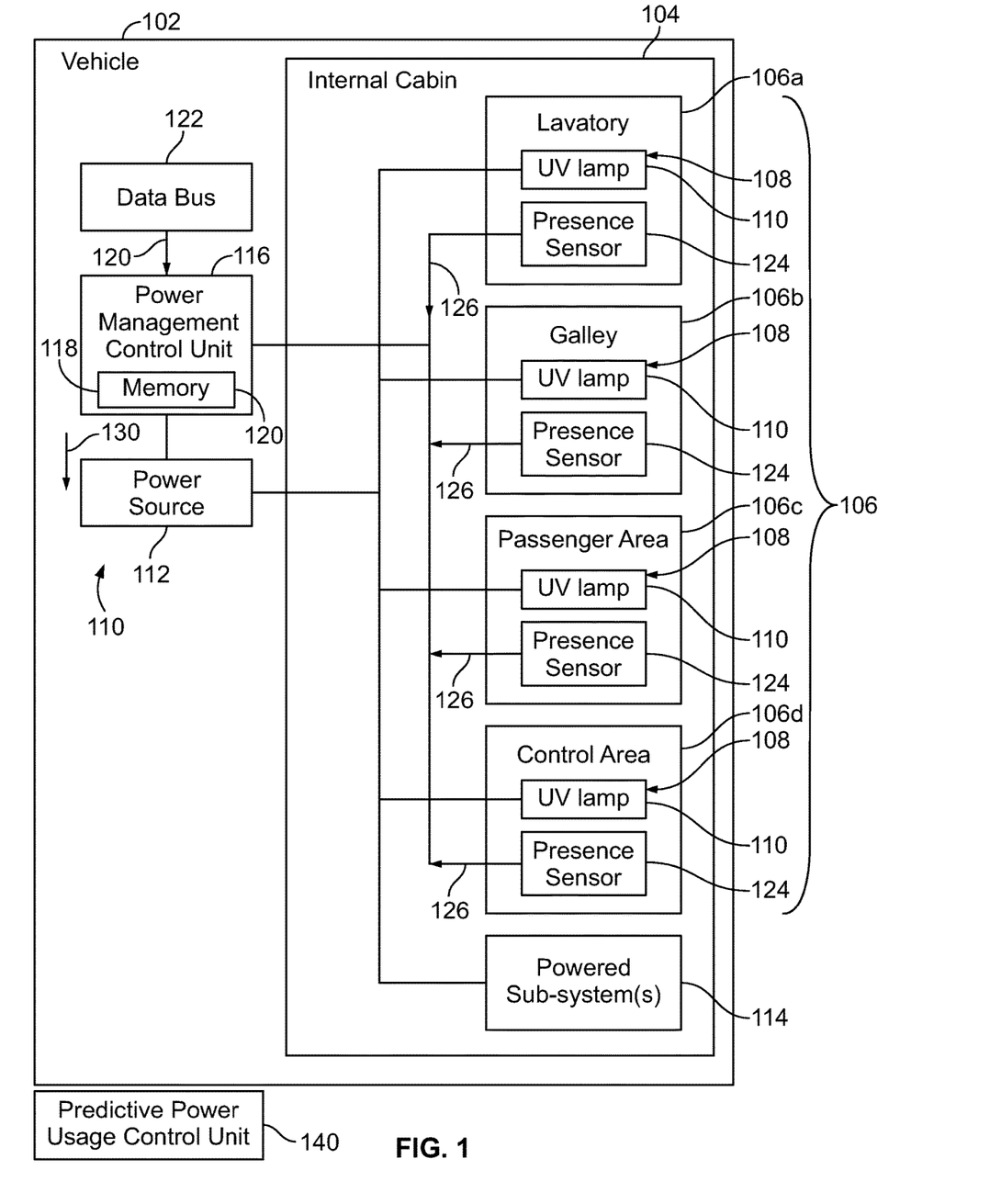
FIG. 1 illustrates a schematic block diagram of a power management system for a vehicle, according to an embodiment of the present disclosure.

FIG. 1 illustrates a schematic block diagram of a power management system 100 for a vehicle 102, according to an embodiment of the present disclosure. While shown with respect to a vehicle, the power management system 100 can be used with various different environments, such as enclosed spaces (such as within residential or commercial buildings), open air venues (such as stadiums), and/or the like. The environment, such as within a vehicle, building, open air stadium, or the like, includes one or more ultraviolet (UV) light sub-systems that are configured to sanitize areas therein.

The environment, such as an internal cabin 104 of the vehicle 102, includes various areas 106 therein. For example, the internal cabin 104 includes a lavatory 106a, a galley 106b, a passenger area 106c (such as where passenger seats are located), a control area 106d (such as a cockpit, flight deck, or the like), and/or the like. The internal cabin 104 can include more or less areas 106 than shown.

One or more of the areas 106 include one or UV light sub-systems 108 that are configured to emit UV light to sanitize components, airflow, or the like therein. Each of the UV light sub-systems 108 includes a UV lamp 110, which is configured to emit the UV light to sanitize one or more portions of the respective area 106. The UV lamp 110 can be configured to emit UV light within the far UV light spectrum, such as at 222 nm. As another example, the UV lamp 110 can be configured to emit UV light within the UVC spectrum, such as at 254 nm.

In at least one embodiment, multiple UV light sub-systems 108 can be in a single area 106. That is, each of the areas 106 can include one or more UV light sub-systems 108. As another example, the internal cabin 104 may include only a single area 106 with a plurality of UV light sub-systems 108.

The UV lamps 110 can be fixed in position. For example, the UV lamps 110 can be secured and fixed to a wall, ceiling, cabinet, or the like. Optionally, the UV lamps 110 can be mobile. For example, the UV lamps 110 can be secured to a structure, and configured to pivot, rotate, articulate, and/or the like. As another example, the UV lamps 110 can be part of portable devices, such as contained within wand assemblies that are coupled to a backpack assembly, a case assembly, a cart assembly, or the like.

The UV lamps 110 of the areas 106 are connected to a power source 112. The power source 112 can be a main or auxiliary source of power within the environment, such as the internal cabin 104 of the vehicle. The power source 112 can be a source of alternating current (AC) power, for example.

In at least one embodiment, the power source 112 is also connected to one or more other powered sub-systems 114 of the internal cabin 104. Examples of the other powered sub-systems 114 include food preparation devices, such as ovens, heaters and air conditioners, audio/video systems (such as in-flight entertainment systems), powered seats, and/or the like. The powered sub-systems 114 may be distributed throughout the internal cabin 104, such as within the various different areas 106.

A power management control unit 116 is in communication with the power source 112, such as through one or more wired or wireless connections. The power management control unit 116 is configured to control the power source 112 (or control power output by the power source 112) to provide power to the UV light sub-systems 110 and the powered sub-system(s) 114 within the internal cabin 104.

In at least one embodiment, the power management control unit 116 is configured to allocate power delivered from the power source 112 to the UV light sub-systems 108 based on need and/or demand. For example, each of the UV lamps 110 has a full capacity power draw. The power management control unit 116 is configured to apportion power to the UV lamps 110 between no power to the full capacity power draw based on the need and/or the demand for the UV lamp 110 at a particular time and in a particular area 106. As an example, during one or more phases of travel (such as takeoff or landing of a commercial aircraft), there may be little to no need for full operation of the UV lamp 110 within a particular area 106, such as the lavatory 106a. As such, the power management control unit 116 may reduce the amount of power supplied to the UV lamp 110 of the lavatory 106a, as the need and/or the demand for the UV lamp 110 within the lavatory 106a at that particular time, may be reduced. Accordingly, the power management control unit 116 can re-direct the saved power (that is, the amount of power reduced to the UV lamp 110 of the lavatory 106a) to other UV lamps 110 within other areas 106, such as the galley 106b, the passenger area 106c, or the control area 106d, and/or to one or more other powered sub-systems 114.

Power usage data 120, such as information regarding the need and/or the demand for power for the UV lamps 110 within different areas 106, the powered sub-systems 114, and/or the like, may be programmed into a memory 118. The power management control unit 116 may include the memory 118. Optionally, the power management control unit 116 may be in communication with the memory 118, such as through one or more wired or wireless connections. As another example, the power usage data 120 may be transmitted from a data bus 122 (such as an avionics data bus) of the vehicle 102. For example, the power usage data 120 can include information regarding a current phase of flight for a commercial aircraft and power needs and/or demands for the various UV lamp 110 and powered sub-systems 114 during such phase. In at least one embodiment, the power management control unit 116 is in communication with the data base 122 through one or more wired or wireless connections.

Based on the power usage data 120, the power management control unit 116 adaptively controls (for example, selectively allocates, apportions, or otherwise varies) the power delivered to the UV light sub-systems 108 and/or the powered sub-systems 114. In at least one embodiment, the power usage data 120 allows the power management control unit 116 to determine power needs for the UV light sub-systems 108 and the powered sub-systems 114 at any given time for the various areas 106 and manage the power delivered among the various UV light-systems 108 and the powered sub-systems 114.

In at least one embodiment, one or more of the areas 106 includes a presence sensor 124, which is configured to detect presence of individuals within the areas 106. Examples of the presence sensors 124 include optical sensors (such as cameras, infrared sensors, or the like), weight sensors (such as electronic scales), thermal sensors, door lock sensors (for example, sensors configured to include when a door is locked and unlocked), and/or the like. The presence sensors 124 are in communication with the power management control unit 116, such as through one or more wired or wireless connections. In at least one embodiment, the presence sensor 124 can be a smart sensor. The presence sensors 124 are in communication with the power management control unit 116 through one or more wired or wireless connections.

The power management control unit 116 receives presence signals 126 output from the presence sensors 124. The presence signals 126 include data indicative of a presence status of the areas 106. Based on the presence signals 126 received from the presence sensors 124, the power management control unit 116 is able to determine a presence status (for example, whether or not an individual is or has been within a particular area) for the areas 106. The power management control unit 116 compares the presence status for the areas 106 with the power usage data 120. For example, if an area 106 is not (or has not been) occupied for a particular, predetermined amount of time, the power management control unit 116 determines that power provided to the UV lamp(s) 110 for such area 106 may be reduced, based on the power usage data 120.

Optionally, not all of the areas 106 may include a presence sensor. Moreover, none of the areas 106 may include presence sensors. Also, alternatively, the power management control unit 116 may not be in communication with presence sensors 124.

As described herein, the power management control unit 116 selectively and adaptively controls an amount of power provided to the UV lamps 110 of the UV light sub-systems 108 of the various areas 106 based on the power usage data 120. The power usage data 120 includes information indicative of a need and/or a demand for power for the UV lamps 110 of the various areas 106 at a particular time. The particular time may be a phase of flight, a detected event that requires UV disinfection (such as movement by one or more individuals within an area 106, a detected sneeze, cough, or a fluid spill within the area 106, and/or the like), etc. The power management control unit 116 apportions power among the UV lamps 110 within the areas 106 (and optionally, the one or more powered sub-systems 114) based on the power usage data 120 regarding the various UV lamps 110 (and optionally, the powered sub-systems 114).

In at least one embodiment, the power management control unit 116 can transmit power management data 130 regarding power management for the various UV lamps 110 (and optionally the powered sub-systems 114) during a predetermined timeframe (such as one or more flights in a day, a week, a month, etc.). The power management data 130 can include information regarding travel between different destinations (such as different airports), time of year, and/or the like.

The power management data 130 is received by a predictive power usage control unit 140, such as may be remote from the vehicle 102 (for example, at a central monitoring station). Optionally, the predictive power usage control unit 140 can be onboard the vehicle 102.

The predictive power usage control unit 140 can receive the power management data 130 from the vehicle 102 and various other vehicles. The predictive power usage control unit 140 can analyze the power management data 130 to determine when and where power requirements differ, such as between different locations, at different times or year, and/or the like. The predictive power usage control unit 140 can then refine the power usage data 120 for a particular trip between different destinations, at different times of year, and/or the like. That is, the predictive power usage control unit 140 is able to aggregate the power management data 130 for various vehicles, for example to further adapt and tailor the power usage data 120 for a particular flight or other such trip (such as if the vehicle 102 is a train or bus).

As described herein, the power management system 100 for an environment, such as the internal cabin 104 of the vehicle 102, includes a plurality of ultraviolet (UV) light sub-systems 108 (each having at least one UV lamp 110) within a plurality of different areas 106 of the internal cabin 104. The power management control unit 116 is in communication with the plurality of UV light sub-systems 108. The power management control unit 116 adaptively controls power supplied to the plurality of UV light sub-systems 108 based on the power usage data 120. The power supplied to the plurality of UV light sub-systems 108 changes. The power usage data 120 includes information regarding adaptable power requirements for the plurality of UV light sub-systems 108. For example, the adaptable power requirements include changing needs for power for the UV light sub-systems 108 over time.

In at least one embodiment, the power management control unit 116 provides a different amount of power to at least two of the plurality of UV light sub-systems at a given time. As an example, the power management control unit 116 adaptively controls the power supplied to the plurality of UV light sub-systems 108 by reducing the power supplied to a first one of the plurality of UV light sub-systems 108 and/or increasing the power supplied to a second one of the plurality of UV light sub-systems 108.

In at least one embodiment, the power management control unit 116 can be in communication with a maintenance control unit through one or more wired or wireless connections. The maintenance control unit can be configured to provide maintenance actions in relation to the power management control unit 116. As another example, the power management control unit 116 can be configured to execute maintenance actions with respect to the UV lamps 110 and/or the presence sensors 124, whether or not a separate maintenance control unit is in communication with the power management control unit 116.

Figure 2:
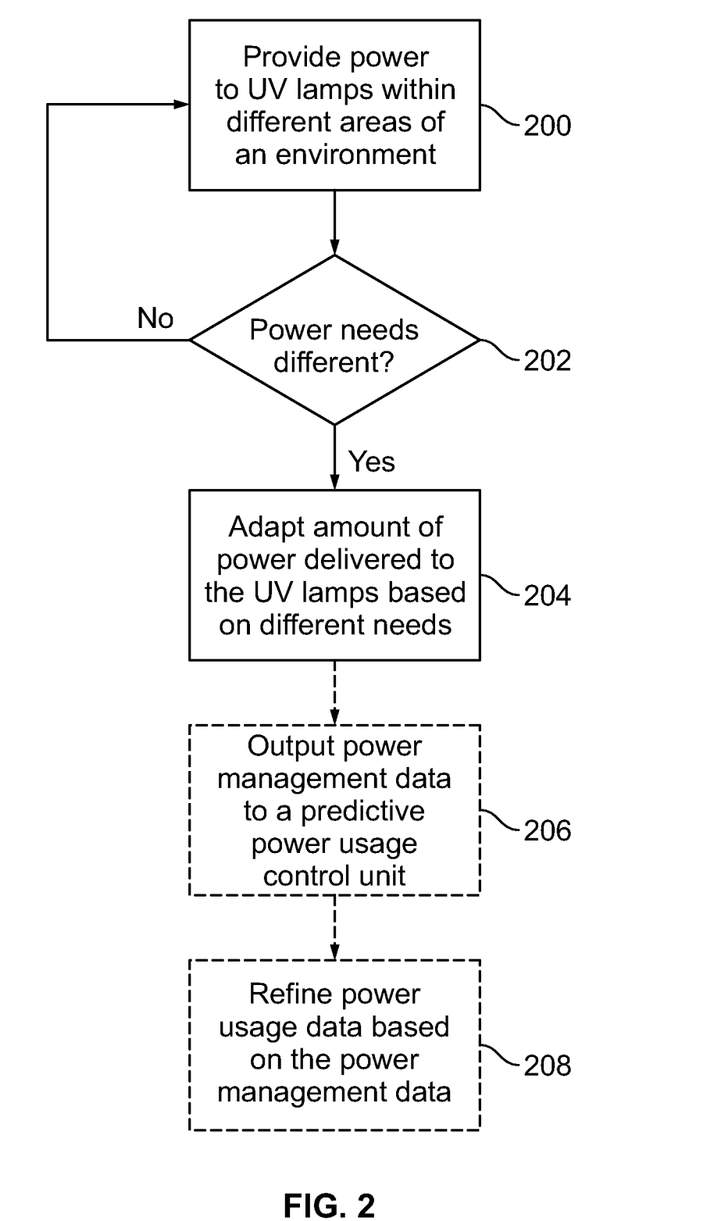
FIG. 2 illustrates a flow chart of a power management method for an environment, according to an embodiment of the present disclosure.

FIG. 2 illustrates a flow chart of a power management method for an environment (such as internal cabin of a vehicle), according to an embodiment of the present disclosure. Referring to FIGS. 1 and 2, the method beings at 200, at which the power source 112 provides power to the UV lamps 110 within the different areas 106 of the environment.

At 202, the power management control unit 116 determines if the power needs for the UV lamps 110 of the areas 106 differ. In at least one embodiment, the power management control unit 116 determines the differing power needs from the power usage data 120. If the power needs do not differ, the method returns to 200, at which the power supplied from the power source 112 can be uniformly provided to the UV lamps 110 (and/or the powered sub-system(s) 114).

If, however, the power needs differ at 202, the power management control unit 116 adapts, at 204, the amount of power delivered to the UV lamps 110 based on the different needs. The selective and adaptive power delivery based on the different needs efficiently allocates power among the UV lamps 110 of the different areas 106.

In at least one optional embodiment, the method may then proceed from 204 to 206, at which the power management control unit 116 outputs the power management data 130 (representative of power management of the various UV lamps 110 and/or the powered sub-system(s) 114 during a predetermined timeframe) to the predictive power usage control unit 140. At 208, the predictive power usage control unit 140 may refine the power usage data 120 based on the power management data 130. Optionally, the method may not include 206 and 208.

As used herein, the term "control unit," "central processing unit," "unit," "CPU," "computer," or the like can include any processor-based or microprocessor-based system including systems using microcontrollers, reduced instruction set computers (RISC), application specific integrated circuits (ASICs), logic circuits, and any other circuit or processor including hardware, software, or a combination thereof capable of executing the functions described herein. Such are exemplary only, and are thus not intended to limit in any way the definition and/or meaning of such terms. For example, the power management control unit 116 and the predictive power usage control unit 140 can be or include one or more processors that are configured to control operation thereof, as described herein.

The power management control unit 116 and the predictive power usage control unit 140 are configured to execute a set of instructions that are stored in one or more data storage units or elements (such as one or more memories), in order to process data. For example, the power management control unit 116 and the predictive power usage control unit 140 can include or be coupled to one or more memories. The data storage units can also store data or other information as desired or needed. The data storage units can be in the form of an information source or a physical memory element within a processing machine. The one or more data storage units or elements can comprise volatile memory or nonvolatile memory, or can include both volatile and nonvolatile memory. As an example, the nonvolatile memory can comprise read only memory (ROM), programmable ROM (PROM), electrically programmable ROM (EPROM), electrically erasable PROM (EEPROM), and/or flash memory and volatile memory can include random access memory (RAM), which can act as external cache memory. The data stores of the disclosed systems and methods is intended to comprise, without being limited to, these and any other suitable types of memory.

The set of instructions can include various commands that instruct the power management control unit 116 and the predictive power usage control unit 140 as a processing machine to perform specific operations such as the methods and processes of the various embodiments of the subject matter described herein. The set of instructions can be in the form of a software program. The software can be in various forms such as system software or application software. Further, the software can be in the form of a collection of separate programs, a program subset within a larger program or a portion of a program. The software can also include modular programming in the form of object-oriented programming. The processing of input data by the processing machine can be in response to user commands, or in response to results of previous processing, or in response to a request made by another processing machine.

The diagrams of embodiments herein illustrate one or more control or processing units, such as the power management control unit 116 and the predictive power usage control unit 140. It is to be understood that the processing or control units can represent circuits, circuitry, or portions thereof that can be implemented as hardware with associated instructions (e.g., software stored on a tangible and non-transitory computer readable storage medium, such as a computer hard drive, ROM, RAM, or the like) that perform the operations described herein. The hardware can include state machine circuitry hardwired to perform the functions described herein. Optionally, the hardware can include electronic circuits that include and/or are connected to one or more logic-based devices, such as microprocessors, processors, controllers, or the like. Optionally, the power management control unit 116 and the predictive power usage control unit 140 can represent processing circuitry such as one or more of a field programmable gate array (FPGA), application specific integrated circuit (ASIC), microprocessor(s), and/or the like. The circuits in various embodiments can be configured to execute one or more algorithms to perform functions described herein. The one or more algorithms can include aspects of embodiments disclosed herein, whether or not expressly identified in a flowchart or a method.

As used herein, the terms "software" and "firmware" are interchangeable, and include any computer program stored in a data storage unit (for example, one or more memories)

for execution by a computer, including RAM memory, ROM memory, EPROM memory, EEPROM memory, and non-volatile RAM (NVRAM) memory. The above data storage unit types are exemplary only, and are thus not limiting as to the types of memory usable for storage of a computer program.

As described herein, embodiments of the present disclosure provide systems and methods for dynamically controlling power supply levels of one or more UV sub-systems 108 in a vehicle 102 or another environment based on various aspects such as human behavior, available power, load shedding, flight route data, aircraft condition, external factors, etc., as contained in the power usage data 120. That is, the power usage data 120 includes information regarding the various aspects.

The UV sub-systems 108 can be installed at various locations within the different areas 106 of the internal cabin 104. The areas 106 can include lavatories, a flight deck, cargo areas, crew rest areas, galleys, assembly areas, passenger seat areas, and the like. As noted, the UV sub-systems 108 may not be operated at 100% or more power capacity at the same time, due to power availability within the internal cabin 104.

Accordingly, the power management control unit 116 is configured to control power delivery to the various UV sub-systems 108 based on need (such as need for UV disinfection) and available power. In at least one embodiment, the power management control unit 116 manages power delivery to the UV sub-systems 108 based on the power usage data 120, which can include information regarding predictions of when and how individual UV sub-systems 108 need to be powered over a particular timeframe.

In terms of predictive aspects, the power usage data 120 can include historical and predictive aircraft condition. For example, when a seat belt sign is on (such as during takeoff and landing), there is no need for UV disinfection within the lavatory 106a (and other common passenger areas).

As another example, the power usage data 120 can include information regarding the particular type of vehicle, such as a particular type of aircraft. Because every airplane is different, and load on the airplane changes on ground and during flight, the power management control unit 116 can adaptively manage power to the UV light sub-systems 108 based on a hierarchy, such as location on plane, available power, and/or the like. Such can be known and/or sensed data from each area 106.

In at least one embodiment, the data bus 122 allows the power management control unit 116 to communicate with various other sub-systems (for example, lighting systems) of the vehicle 102. The power management control unit 116 can predict how and when to control power to the UV light sub-systems 108 based on other power loads (for example, if it is known or predicted that microwaves within the galley(s) 106b may be used at once), for a more uniform power distribution for the UV light sub-systems 108. The predictions can be dynamic and based on external factors, such as an existing pandemic, flight routes and changes thereof, and/or the like. Using the prediction, the power management control unit 116 can proactively control the UV light sub-systems 108, such as if they need to catch up on disinfection before reducing power to UV lamps 110 within certain areas 106.

In at least one embodiment, the power management control unit 116 and/or another control unit in communication with the power management control unit 116 via the data bus 122 can monitor generator load of the vehicle 102. The power management control unit 116 can use the generator load to know when power is or is not going to be available for various sub-systems of the vehicle 102. As an example, one or more UV light subsystems 108 can use some or all of the last remaining portion of the generator load prior to the airplane shedding the last remaining portion. Such can be done proportionately, for instance, by changing the power supplied to one or more UV light sub-systems 108 that may need any available power at a certain time (for example, just after flight crew beverage/food service). The power management control unit 116 (or other control unit in communication with the power management control unit 116) can predict what the generator load would be, and then adjust the UV light sub-systems 108 to be within the predicted generator load, which can be performed via a hierarchy within the UV light sub-systems 108 (for example, at a first time, such as during cruise, and after meal service), the UV light sub-system 108 within the lavatory 106a may be at the top of the hierarchy list, and then cabin, galleys, crew rest, flight deck, and the like may follow according the hierarchy. The hierarchy, which can be stored in the memory 118 and/or part of the power usage data 120, can be dynamic based on a variety of factors regarding flight condition, route, time of day, season, and/or the like. Predictive correlations over time can be observed (for example, lavatory use, galley use, etc.), and controlled accordingly.

In at least one embodiment, the UV light sub-systems 108 can be configured to negotiate with the power management control unit 116. For example, the UV light sub-systems 108 can include control units that negotiate with the power management control unit 116 with respect to supplied power based on known or predictive power loads. For example, all of the UV light sub-systems 108 and the powered sub-systems 114 can be in communication with one another through one or more wired or wireless connections. As such, the various sub-systems 108 and 114 are able to determine the power needed for each other, and negotiate with the power management control unit 116 accordingly. As an example, each of the various sub-systems 108 and 114 can negotiate through outputting signals regarding overall power need, a predetermined lower power backup request, and/or the like. The power management control unit 116 can assess such negotiations and apportion power based on overall power availability, order of requests, priority for certain areas, and/or the like. Because the power management control unit 116 can predict when various loads and sub-systems will be utilized, the power management control unit 116 can control the various UV light systems 108 accordingly.

In at least one embodiment, the power usage data 120 may include a prioritized list for powering essential and nonessential sub-systems. The prioritized list can be predetermined and fixed. Optionally, the prioritized list can change over time. With respect to nonessential sub-systems, priority can be changed based on certain conditions. As an example, the power management control unit 116 can adapt a prioritized list of power delivery for various non-essential sub-systems, such as UV light sub-systems 108 within different areas, meal preparation sub-systems, entertainment sub-systems, and/or the like.

Depending on a particular UV light sub-system 108 and location, there may be a lower limit of power needed at various times. The power usage data 120 can include such information, and allocate power accordingly. As an example, a UV lamp 108 can be powered below or above 100% preferred capacity, depending on the situation, such as when the power management control unit 116 determines, via a respective presence sensor 124, that an individual is walking into or out of the lavatory 106*a*, and therefore the lavatory 106*a* likely needs cleaning. As such, the power management control unit 116 can ensure that the UV lamp 110 within the lavatory 106*a* is overpowered quickly, along with considering a thermal limit or predictive thermal limit (and based on known, prior usage), to attain provide a quick disinfection before the individual arrives at the lavatory 106*a*.

Photo sensors within the areas 106 can measure the UV light emitted by the UV lamps 110, and then transmit data to the power management control unit 116 and/or another control unit of the vehicle for analysis by an artificial intelligence/machine learning system. Such system can analyze information regarding delays, turn times, flight routes, UV system usage inflight, and/or the like.

Predictive maintenance can be another aspect of data to capture on or offboard. Data for scheduled events can be analyzed by the power management control unit 116 to control UV light systems 108 (and other powered sub-systems 114), such as any number events like seatbelt sign, mealtime, and/or the like. For example, the power management system 116 can selectively activate and deactivate UV lamps 110 such as for higher loads after meals (which can be determined based on the oven usage, for example).

In general, the power management control unit 116 is configured to adaptively control power delivered to the UV light sub-systems 108 and the powered sub-system(s) 114 based on various aspects, characteristics, predictions, and the like.

Figure 3:
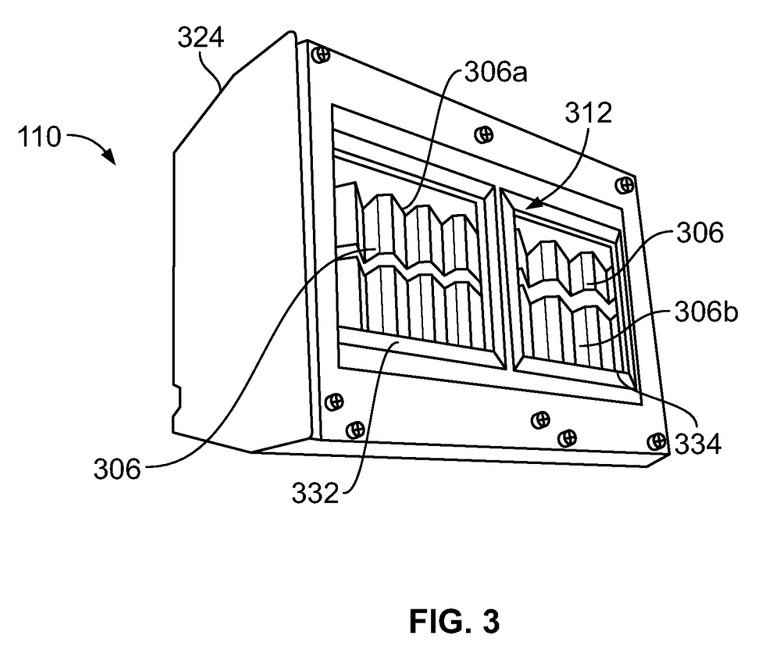
FIG. 3 illustrates a perspective view of a first side of a UV lamp, according to an embodiment of the present disclosure.

FIG. 3 illustrates a perspective view of a first side (such as a bottom or top) of a UV lamp 110, according to an embodiment of the present disclosure. The UV lamp 110 includes a housing 324 that retains a plurality of UV light emitters 306 that are configured to emit UV light through an aperture 312. As shown, the UV lamp 110 includes a first plurality of UV light emitters 306*a* and a second plurality of UV light emitters 306*b*. The first plurality of UV light emitters 306*a* are contained within a first sub-housing 332, and the second plurality of UV light emitters 306*b* are contained within a second sub-housing 334 that is distinct from the first sub-housing 332. Each of the first sub-housing 332 and the second sub-housing 334 can contain more or less UV light emitters 306 than shown. Optionally, the UV lamp 110 can include a single sub-housing that retains all of the UV light emitters 306. In at least one embodiment, the UV lamp 110 can include a single UV light emitter 306, instead a plurality of UV light emitters 306. The UV lamp 110 shown in FIG. 3 is merely an example. The UV lamp 110 can be sized and shaped differently than shown in FIG. 3.

Figure 4:
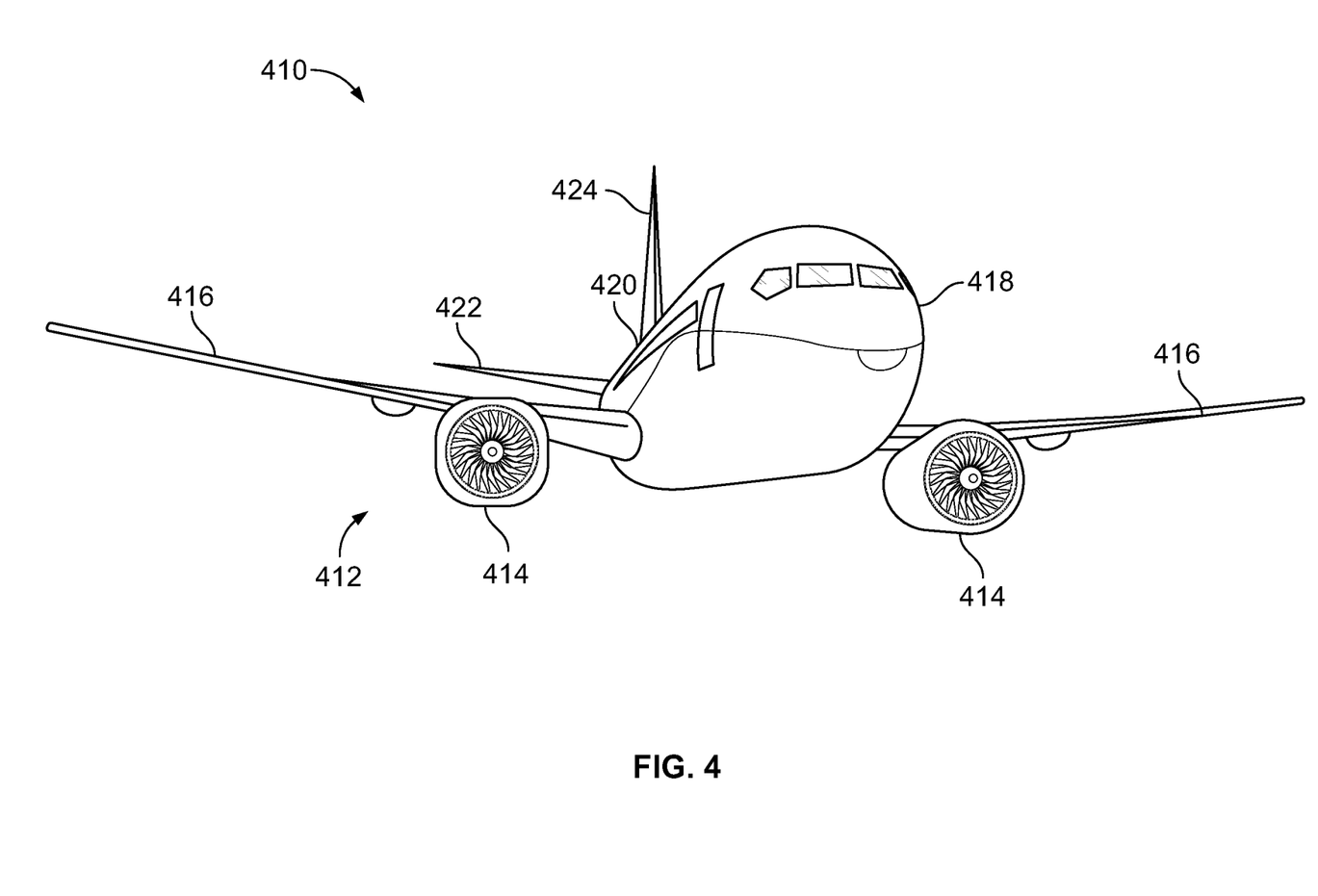
FIG. 4 illustrates a perspective front view of an aircraft, according to an embodiment of the present disclosure.

FIG. 4 illustrates a perspective front view of an aircraft 410, according to an embodiment of the present disclosure. The aircraft 410 includes a propulsion system 412 that includes engines 414, for example. Optionally, the propulsion system 412 may include more engines 414 than shown. The engines 414 are carried by wings 416 of the aircraft 410. In other embodiments, the engines 414 may be carried by a fuselage 418 and/or an empennage 420. The empennage 420 may also support horizontal stabilizers 422 and a vertical stabilizer 424.

The fuselage 418 of the aircraft 410 defines an internal cabin 430, which includes a flight deck or cockpit, one or more work sections (for example, galleys, personnel carry-on baggage areas, and the like), one or more passenger sections (for example, first class, business class, and coach sections), one or more lavatories, and/or the like. The internal cabin 430 is an example of the environment, such as the internal cabin 104 shown in FIG. 1.

Embodiments of the present disclosure are used within the internal cabin 430. Alternatively, instead of an aircraft, embodiments of the present disclosure may be used with various other vehicles, such as automobiles, buses, locomotives and train cars, watercraft, and the like. Further, embodiments of the present disclosure may be used with respect to fixed structures, such as commercial and residential buildings.

Figure 5A:
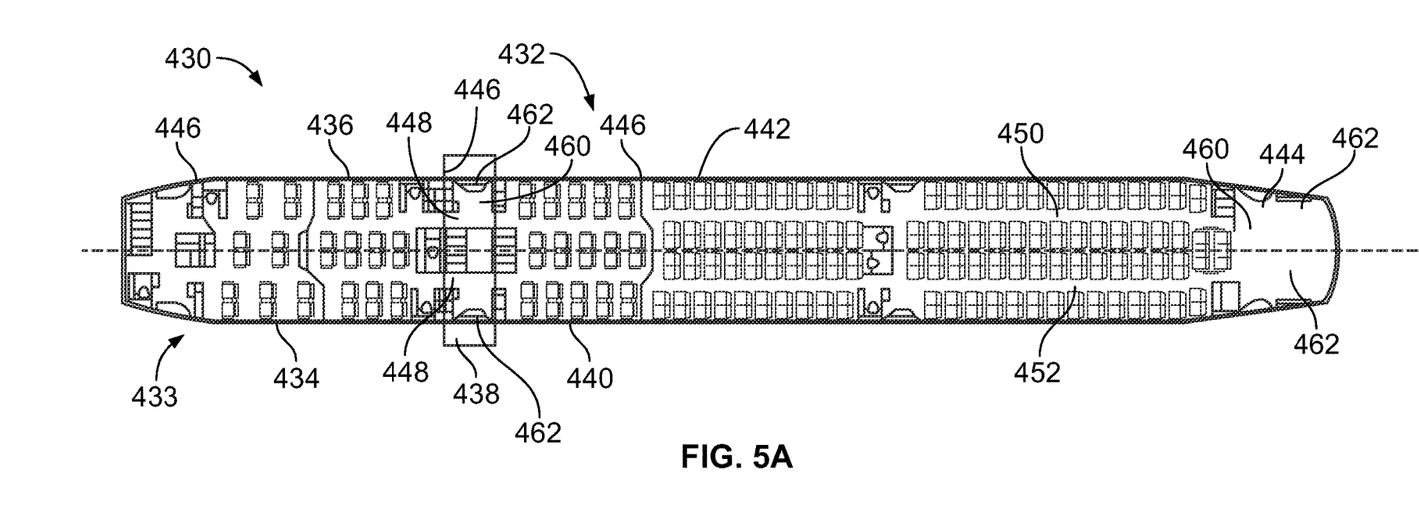
FIG. 5A illustrates a top plan view of an internal cabin of an aircraft, according to an embodiment of the present disclosure.

FIG. 5A illustrates a top plan view of an internal cabin 430 of an aircraft, according to an embodiment of the present disclosure. The internal cabin 430 may be within the fuselage 432 of the aircraft, such as the fuselage 418 of FIG. 4. For example, one or more fuselage walls may define the internal cabin 430. The internal cabin 430 includes multiple sections, including a front section 433, a first class section 434, a business class section 436, a front galley station 438, an expanded economy or coach section 440, a standard economy of coach section 442, and an aft section 444, which may include multiple lavatories and galley stations. It is to be understood that the internal cabin 430 may include more or less sections than shown. For example, the internal cabin 430 may not include a first class section, and may include more or less galley stations than shown. Each of the sections may be separated by a cabin transition area 446, which may include class divider assemblies between aisles 448.

As shown in FIG. 5A, the internal cabin 430 includes two aisles 450 and 452 that lead to the aft section 444. Optionally, the internal cabin 430 may have less or more aisles than shown. For example, the internal cabin 430 may include a single aisle that extends through the center of the internal cabin 430 that leads to the aft section 444.

The aisles 448, 450, and 452 extend to egress paths or door passageways 460. Exit doors 462 are located at ends of the egress paths 460. The egress paths 460 may be perpendicular to the aisles 448, 450, and 452. The internal cabin 430 may include more egress paths 460 at different locations than shown. Embodiments of the present disclosure shown and described with respect to FIGS. 1-2 may be used within the internal cabin 430.

Figure 5B:
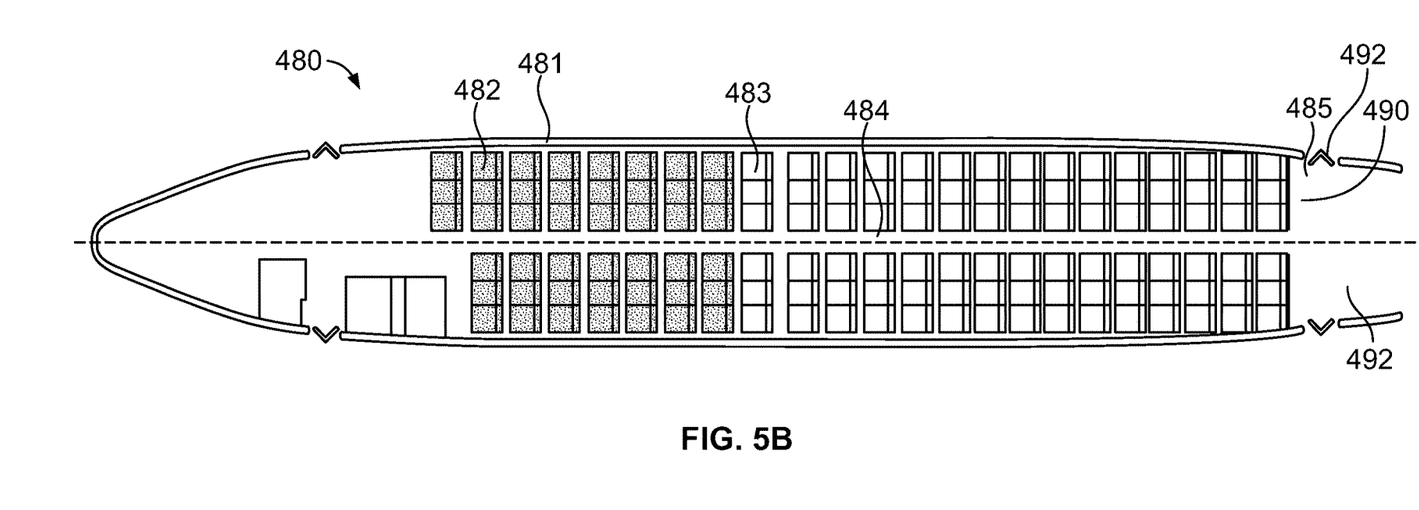
FIG. 5B illustrates a top plan view of an internal cabin of an aircraft, according to an embodiment of the present disclosure.

FIG. 5B illustrates a top plan view of an internal cabin 480 of an aircraft, according to an embodiment of the present disclosure. The internal cabin 480 is an example of the internal cabin 430 shown in FIG. 4. The internal cabin 480 may be within a fuselage 481 of the aircraft. For example, one or more fuselage walls may define the internal cabin 480. The internal cabin 480 includes multiple sections, including a main cabin 482 having passenger seats 483, and an aft section 485 behind the main cabin 482. It is to be understood that the internal cabin 480 may include more or less sections than shown.

The internal cabin 480 may include a single aisle 484 that leads to the aft section 485. The single aisle 484 may extend through the center of the internal cabin 480 that leads to the aft section 485. For example, the single aisle 484 may be coaxially aligned with a central longitudinal plane of the internal cabin 480.

The aisle 484 extends to an egress path or door passageway 490. Exit doors 492 are located at ends of the egress path 490. The egress path 490 may be perpendicular to the aisle 484. The internal cabin 480 may include more egress paths than shown. Embodiments of the present disclosure shown and described with respect to FIGS. 1-2 may be used within the internal cabin 480.

Figure 6:
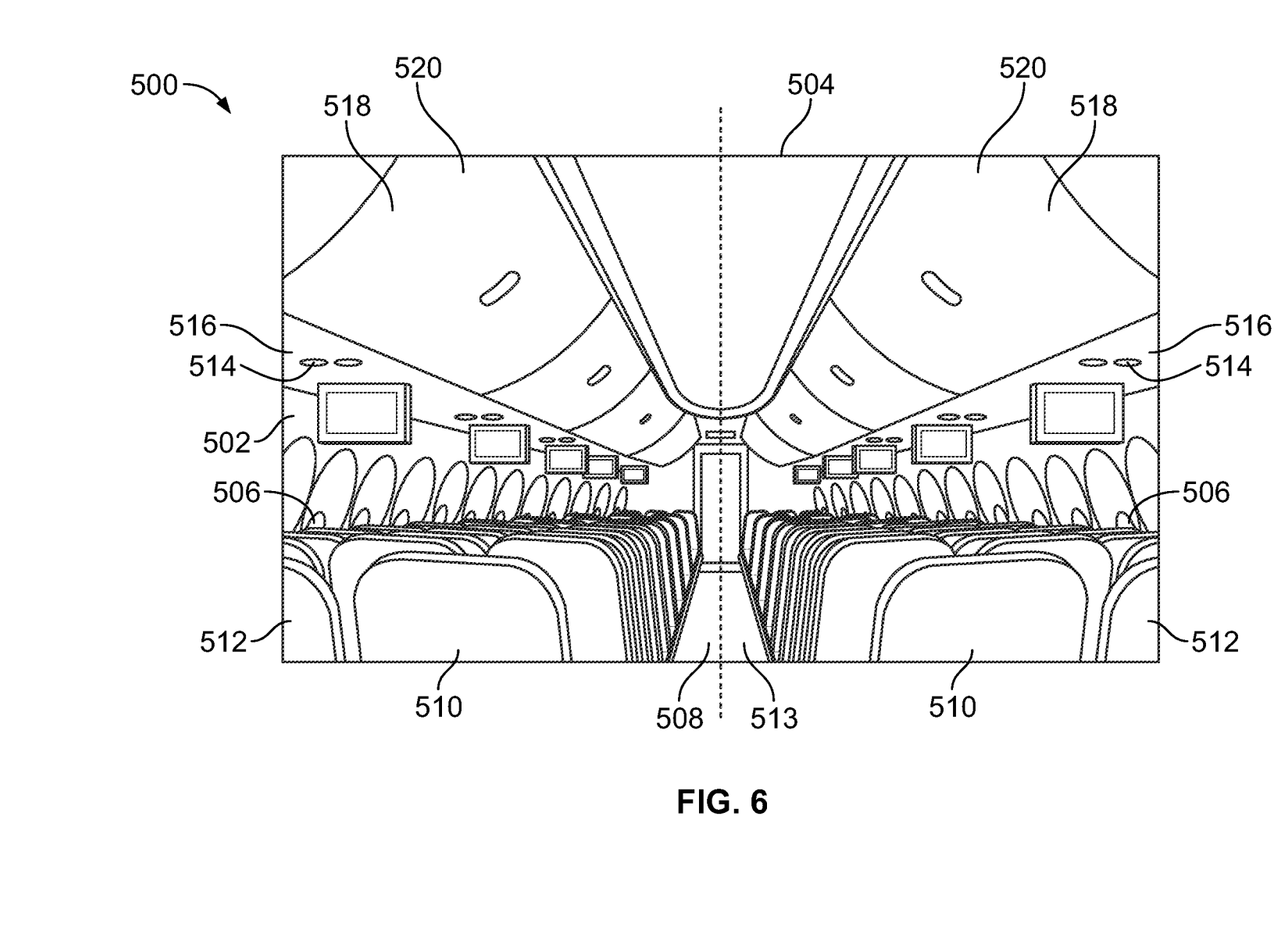
FIG. 6 illustrates a perspective interior view of an internal cabin of an aircraft, according to an embodiment of the present disclosure.

FIG. 6 illustrates a perspective interior view of an internal cabin 500 of an aircraft, according to an embodiment of the present disclosure. The internal cabin 500 includes outboard walls 502 connected to a ceiling 504. Windows 506 may be formed within the outboard walls 502. A floor 508 supports rows of seats 510. As shown in FIG. 10, a row 512 may include two seats 510 on either side of an aisle 513. However, the row 512 may include more or less seats 510 than shown. Additionally, the internal cabin 500 may include more aisles than shown.

Passenger service units (PSUs) 514 are secured between an outboard wall 502 and the ceiling 504 on either side of the aisle 513. The PSUs 514 extend between a front end and rear end of the internal cabin 500. For example, a PSU 514 may be positioned over each seat 510 within a row 512. Each PSU 514 may include a housing 516 that generally contains vents, reading lights, an oxygen bag drop panel, an attendant request button, and other such controls over each seat 510 (or groups of seats) within a row 512.

Overhead stowage bin assemblies 518 are secured to the ceiling 504 and/or the outboard wall 502 above and inboard from the PSU 514 on either side of the aisle 513. The overhead stowage bin assemblies 518 are secured over the seats 510. The overhead stowage bin assemblies 518 extend between the front and rear end of the internal cabin 500. Each stowage bin assembly 518 may include a pivot bin or bucket 520 pivotally secured to a strongback (hidden from view in FIG. 6). The overhead stowage bin assemblies 518 may be positioned above and inboard from lower surfaces of the PSUs 514. The overhead stowage bin assemblies 518 are configured to be pivoted open in order to receive passenger carry-on baggage and personal items, for example.

Embodiments of the present disclosure shown and described with respect to FIGS. 1-2 can be used in the internal cabin 500. The internal cabin 500 is an example of an environment, such as the internal cabin 104 shown in FIG. 1.

Further, the disclosure comprises embodiments according to the following clauses:

Clause 1. A power management system for a vehicle, the power management system comprising:
   a plurality of ultraviolet (UV) light sub-systems within an internal cabin of the vehicle; and
   a power management control unit in communication with the plurality of UV light sub-systems,
   wherein the power management control unit is configured to adaptively control power supplied to the plurality of UV light sub-systems based on power usage data, wherein the power supplied to the plurality of UV light sub-systems changes, and wherein the power usage data includes information regarding adaptable power requirements for the plurality of UV light sub-systems.

Clause 2. The power management system of Clause 1, wherein the power management control unit is configured to provide a different amount of power to at least two of the plurality of UV light sub-systems at a given time.

Clause 3. The power management system of Clauses 1 or 2, wherein the plurality of UV light sub-systems are within a plurality of different areas of the internal cabin, and wherein the plurality of different areas comprise one or more of a lavatory, a galley, a passenger area, or a control area.

Clause 4. The power management system of any of Clauses 1-3, further comprising one or more powered sub-systems that differ from the UV light sub-systems.

Clause 5. The power management system of Clause 4, wherein the power management control unit is also in communication with the one or more powered sub-systems, and wherein the power management control unit also adaptively controls power supplied to the one or more powered sub-systems.

Clause 6. The power management system of any of Clauses 1-5, wherein the power management control unit adaptively controls the power supplied to the plurality of UV light sub-systems by one or both of reducing the power supplied to a first one of the plurality of UV light sub-systems or increasing the power supplied to a second one of the plurality of UV light sub-systems.

Clause 7. The power management system of any of Clauses 1-6, further comprising a data bus in communication with the power management control unit, wherein the power management control unit receives the power usage data from the data bus.

Clause 8. The power management system of any of Clauses 1-7, further comprising one or more presence sensors within one or more of the plurality of areas, wherein the power management control unit is in communication with the one or more presence sensors, and wherein the power management control unit adaptively controls the power supplied to the plurality of UV light sub-systems based on the power usage data and one or more presence signals received from the one or more presence sensors.

Clause 9. The power management system of any of Clauses 1-8, further comprising a predictive power usage control unit in communication with the power management control unit, wherein the predict power usage control unit receives power management data from the power management control unit, and wherein the predictive power usage control unit is configured to refine the power usage data based on the power management data.

Clause 10. The power management system of Clause 9, wherein the predictive power usage control unit is remote from the vehicle.

Clause 11. The power management system of any of Clauses 1-10, wherein the power usage data comprises a prioritized list for powering essential and nonessential sub-systems.

Clause 12. A power management method for a vehicle, the power management method comprising:
   communicatively coupling a power management control unit with a plurality of ultraviolet (UV) light sub-systems within an internal cabin of the vehicle; and
   adaptively controlling, by the power management control unit, power supplied to the plurality of UV light sub-systems based on power usage data, wherein the power supplied to the plurality of UV light sub-systems changes, and wherein the power usage data includes information regarding adaptable power requirements for the plurality of UV light sub-systems.

Clause 13. The power management method of Clause 12, wherein said adaptively controlling comprises providing a different amount of power to at least two of the plurality of UV light sub-systems at a given time.

Clause 14. The power management method of Clauses 12 or 13, wherein the plurality of different areas comprise one or more of a lavatory, a galley, a passenger area, or a control area.

Clause 15. The power management method of any of Clauses 12-14, further comprising:
   communicatively coupling the power management control unit with one or more powered sub-systems that differ from the UV light sub-systems; and
   adaptively controlling, by the power management control unit, power supplied to the one or more powered sub-systems.

Clause 16. The power management method of any of Clauses 12-15, wherein said adaptively controlling comprises one or both of reducing the power supplied to a first one of the plurality of UV light sub-systems or increasing the power supplied to a second one of the plurality of UV light sub-systems.

Clause 17. The power management method of any of Clauses 12-16, further comprising:
communicatively coupling a data bus with the power management control unit; and
receiving, by the power management control unit, the power usage data from the data bus.

Clause 18. The power management method of any of Clauses 12-17, further comprising:
communicatively coupling the power management control unit with one or more presence sensors within one or more of the plurality of areas; and
adaptively controlling the power supplied to the plurality of UV light sub-systems based on the power usage data and one or more presence signals received from the one or more presence sensors.

Clause 19. The power management method of any of Clauses 12-18, further comprising:
communicatively coupling the power management control unit with a predictive power usage control unit;
receiving, by the predictive power usage control unit, power management data from the power management control unit; and
refining, by the predictive power usage control unit, the power usage data based on the power management data.

Clause 20. The power management method of any of Clauses 12-19, wherein the power usage data comprises a prioritized list for powering essential and nonessential sub-systems.

Clause 21. A power management system for an aircraft, the power management system comprising:
a plurality of ultraviolet (UV) light sub-systems within a plurality of different areas of an internal cabin of the aircraft, wherein the plurality of different areas comprise one or more of a lavatory, a galley, a passenger area, or a control area;
one or more powered sub-systems that differ from the UV light sub-systems; and
a power management control unit in communication with the plurality of UV light sub-systems and the one or more powered sub-systems,
wherein the power management control unit is configured to adaptively control power supplied to the plurality of UV light sub-systems and the one or more powered sub-systems based on power usage data, wherein the power supplied to one or both of the plurality of UV light sub-systems or the one or more powered sub-systems changes, wherein the power usage data includes information regarding adaptable power requirements for the plurality of UV light sub-systems, wherein the power management control unit is configured to provide a different amount of power to at least two of the plurality of UV light sub-systems at a given time, and wherein the power management control unit adaptively controls the power supplied to the plurality of UV light sub-systems by one or both of reducing the power supplied to a first one of the plurality of UV light sub-systems or increasing the power supplied to a second one of the plurality of UV light sub-systems.

Clause 22. The power management system of Clause 21, further comprising a data bus in communication with the power management control unit, wherein the power management control unit receives the power usage data from the data bus.

Clause 23. The power management system of Clauses 21 or 22, further comprising one or more presence sensors within one or more of the plurality of areas, wherein the power management control unit is in communication with the one or more presence sensors, and wherein the power management control unit adaptively controls the power supplied to the plurality of UV light sub-systems based on the power usage data and one or more presence signals received from the one or more presence sensors.

Clause 24. The power management system of any of Clauses 21-23, further comprising a predictive power usage control unit in communication with the power management control unit, wherein the predictive power usage control unit receives power management data from the power management control unit, and wherein the predictive power usage control unit is configured to refine the power usage data based on the power management data.

Clause 25. The power management system of any of Clauses 21-24, wherein the power usage data comprises a prioritized list for powering essential and nonessential sub-systems.

Clause 26. A power management system for a vehicle, the power management system comprising:
a plurality of ultraviolet (UV) light sub-systems within an internal cabin of the vehicle, wherein UV light sub-systems are configured to be provided power based on power usage data, wherein the power usage data includes information regarding adaptable power requirements for the plurality of UV light sub-systems; and
a predictive power usage control unit configured to receive power management data, wherein the predictive power usage control unit is further configured to refine the power usage data based on the power management data.

As described herein, embodiments of the present disclosure provide systems and methods for managing power among UV lamps and other powered sub-systems of a vehicle. Further, embodiments of the present disclosure provide systems and methods for efficiently and effectively apportioning power to various powered sub-systems and UV lamps of a vehicle.

While various spatial and directional terms, such as top, bottom, lower, mid, lateral, horizontal, vertical, front and the like can be used to describe embodiments of the present disclosure, it is understood that such terms are merely used with respect to the orientations shown in the drawings. The orientations can be inverted, rotated, or otherwise changed, such that an upper portion is a lower portion, and vice versa, horizontal becomes vertical, and the like.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

It is to be understood that the above description is intended to be illustrative, and not restrictive. For example, the above-described embodiments (and/or aspects thereof) can be used in combination with each other. In addition, many modifications can be made to adapt a particular situation or material to the teachings of the various embodiments of the disclosure without departing from their scope. While the dimensions and types of materials described herein are intended to define the parameters of the various embodiments of the disclosure, the embodiments are by no means limiting and are exemplary embodiments. Many other embodiments will be apparent to those of skill in the art upon reviewing the above description. The scope of the various embodiments of the disclosure should, therefore, be determined with reference to the appended claims, along with the full scope of equivalents to which such claims are entitled. In the appended claims and the detailed description herein, the terms "including" and "in which" are used as the plain-English equivalents of the respective terms "comprising" and "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments of the disclosure, including the best mode, and also to enable any person skilled in the art to practice the various embodiments of the disclosure, including making and using any devices or systems and performing any incorporated methods. The patentable scope of the various embodiments of the disclosure is defined by the claims, and can include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A power management system for a vehicle, the power management system comprising:
    a plurality of ultraviolet (UV) light sub-systems within an internal cabin of the vehicle; and
    a power management control unit in communication with the plurality of UV light sub-systems,
    wherein the power management control unit is configured to adaptively control power supplied to the plurality of UV light sub-systems based on power usage data, and wherein the power usage data includes: information regarding adaptable power requirements for the plurality of UV light sub-systems, and a prioritized list for powering essential and nonessential sub-systems.

2. The power management system of claim 1, wherein the power management control unit is configured to provide a different amount of power to at least two of the plurality of UV light sub-systems at a given time.

3. The power management system of claim 1, wherein the plurality of UV light sub-systems are within a plurality of different areas of the internal cabin, and wherein the plurality of different areas comprise one or more of a lavatory, a galley, a passenger area, or a control area.

4. The power management system of claim 1, further comprising one or more powered sub-systems that differ from the UV light sub-systems.

5. The power management system of claim 4, wherein the power management control unit is also in communication with the one or more powered sub-systems, and wherein the power management control unit also adaptively controls power supplied to the one or more powered sub-systems.

6. The power management system of claim 1, wherein the power management control unit adaptively controls the power supplied to the plurality of UV light sub-systems by one or both of reducing the power supplied to a first one of the plurality of UV light sub-systems or increasing the power supplied to a second one of the plurality of UV light sub-systems.

7. The power management system of claim 1, further comprising a data bus in communication with the power management control unit, wherein the power management control unit receives the power usage data from the data bus.

8. The power management system of claim 1, further comprising one or more presence sensors within one or more of the plurality of areas, wherein the power management control unit is in communication with the one or more presence sensors, and wherein the power management control unit adaptively controls the power supplied to the plurality of UV light sub-systems based on the power usage data and one or more presence signals received from the one or more presence sensors.

9. The power management system of claim 1, further comprising a predictive power usage control unit in communication with the power management control unit, wherein the predictive power usage control unit receives power management data from the power management control unit, and wherein the predictive power usage control unit is configured to refine the power usage data based on the power management data.

10. The power management system of claim 9, wherein the predictive power usage control unit is remote from the vehicle.

11. The power management system of claim 1, wherein the prioritized list changes over time.

12. The power management system of claim 1, wherein the prioritized list is predetermined and fixed.

13. A power management method for a vehicle, the power management method comprising:
    communicatively coupling a power management control unit with a plurality of ultraviolet (UV) light sub-systems within an internal cabin of the vehicle; and
    adaptively controlling, by the power management control unit, power supplied to the plurality of UV light sub-systems based on power usage data, wherein the power usage data includes: information regarding adaptable power requirements for the plurality of UV light sub-systems, and a prioritized list for powering essential and nonessential sub-systems.

14. The power management method of claim 13, wherein said adaptively controlling comprises providing a different amount of power to at least two of the plurality of UV light sub-systems at a given time.

15. The power management method of claim 13, wherein the plurality of UV light sub-systems are within a plurality of different areas of the internal cabin, and wherein the plurality of different areas comprise one or more of a lavatory, a galley, a passenger area, or a control area.

16. The power management method of claim 13, further comprising:
    communicatively coupling the power management control unit with one or more powered sub-systems that differ from the UV light sub-systems; and
    adaptively controlling, by the power management control unit, power supplied to the one or more powered sub-systems.

17. The power management method of claim 13, wherein said adaptively controlling comprises one or both of reducing the power supplied to a first one of the plurality of UV light sub-systems or increasing the power supplied to a second one of the plurality of UV light sub-systems.

18. The power management method of claim 13, further comprising:
   communicatively coupling a data bus with the power management control unit; and
   receiving, by the power management control unit, the power usage data from the data bus.

19. The power management method of claim 13, further comprising:
   communicatively coupling the power management control unit with one or more presence sensors within one or more of the plurality of areas; and
   adaptively controlling the power supplied to the plurality of UV light sub-systems based on the power usage data and one or more presence signals received from the one or more presence sensors.

20. The power management method of claim 13, further comprising:
   communicatively coupling the power management control unit with a predictive power usage control unit;
   receiving, by the predictive power usage control unit, power management data from the power management control unit; and
   refining, by the predictive power usage control unit, the power usage data based on the power management data.

21. A power management system for an aircraft, the power management system comprising:
   a plurality of ultraviolet (UV) light sub-systems within an internal cabin of the aircraft;
   one or more powered sub-systems that differ from the UV light sub-systems; and
   a power management control unit in communication with the plurality of UV light sub-systems and the one or more powered sub-systems,
   wherein the power management control unit is configured to adaptively control power supplied to the plurality of UV light sub-systems and the one or more powered sub-systems based on power usage data, wherein the power supplied to one or both of the plurality of UV light sub-systems or the one or more powered sub-systems changes, wherein the power usage data includes: (a) information regarding adaptable power requirements for the plurality of UV light sub-systems, and (b) a prioritized list for powering essential and nonessential sub-systems, wherein the power management control unit is configured to provide a different amount of power to at least two of the plurality of UV light sub-systems at a given time, and wherein the power management control unit adaptively controls the power supplied to the plurality of UV light sub-systems by one or both of reducing the power supplied to a first one of the plurality of UV light sub-systems or increasing the power supplied to a second one of the plurality of UV light sub-systems.

22. A power management system for a vehicle, the power management system comprising:
   a plurality of ultraviolet (UV) light sub-systems within an internal cabin of the vehicle, wherein the UV light sub-systems are configured to be provided power based on power usage data, wherein the power usage data includes: information regarding adaptable power requirements for the plurality of UV light sub-systems, and a prioritized list for powering essential and nonessential sub-systems; and
   a predictive power usage control unit configured to receive power management data, wherein the predictive power usage control unit is further configured to refine the power usage data based on the power management data.

* * * * *